(12) United States Patent
Behnam

(10) Patent No.: US 6,774,247 B2
(45) Date of Patent: Aug. 10, 2004

(54) AQUEOUS SOLUTION OF ASCORBIC ACID AND METHOD FOR PRODUCING SAME

(75) Inventor: Dariush Behnam, Rossdorf (DE)

(73) Assignee: AquaNova German Solubilisate Technology (AGT) GmbH, Darmstadt (DE)

(*) Notice: Subject to any disclaimer, the term of this patent is extended or adjusted under 35 U.S.C. 154(b) by 0 days.

(21) Appl. No.: 10/307,288

(22) Filed: Dec. 2, 2002

(65) Prior Publication Data

US 2003/0105157 A1 Jun. 5, 2003

(30) Foreign Application Priority Data

Nov. 30, 2001 (DE) .......................... 101 58 447

(51) Int. Cl.$^7$ .......................................... C07D 305/12
(52) U.S. Cl. ...................................................... 549/315
(58) Field of Search ........................................ 549/315

(56) References Cited

U.S. PATENT DOCUMENTS

| 3,249,504 A | 5/1966 | Cappel et al. |
| 5,607,707 A | 3/1997 | Ford et al. |
| 5,656,289 A | 7/1997 | Cho et al. |

FOREIGN PATENT DOCUMENTS

| EP | 0352375 | 1/1990 |
| EP | 0440398 | 8/1991 |
| EP | 0821950 | 2/1998 |
| EP | 0956779 | 11/1999 |
| GB | 780886 | 8/1957 |
| WO | 9406310 | 3/1994 |
| WO | 9939580 | 8/1999 |
| WO | 0243719 | 6/2002 |

OTHER PUBLICATIONS

Rolland I Poust et al., "Copper–Catalyzed Oxidation of Ascorbic Acid in Gels and Aqueous Solutions of Polysorbate 80", Journal of Pharmaceutical Sciences, vol. 57, No. 12, Dec. 1968, pp. 2119–2125.

Primary Examiner—Amelia Owens
(74) Attorney, Agent, or Firm—Jacobson Holman PLLC

(57) ABSTRACT

Disclosed is an aqueous solution of ascorbic acid which contains an excess of an emulsifier with an HLB value of about 9 to about 18, for example a polysorbate, a method of manufacture of such solution and applications thereof.

17 Claims, 4 Drawing Sheets

Product Micelle of Vitamin C

For the first time, it has been possible to observe the product micelle through electron microscope photographs (carried out at the Technical University of Darmstadt, commissioned by AQUANOVA).

Vitamin C micelle of liquid, stabilised ascorbic acid:

10% ascorbic acid solubilisate, diluted 1 : 1000.

a) in water

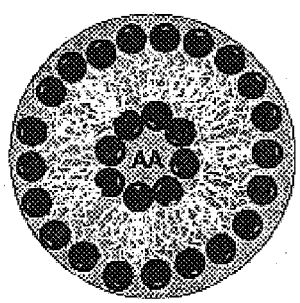
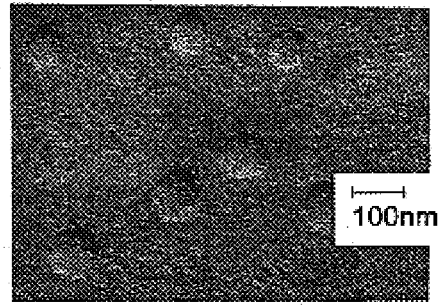

b) in paraffin

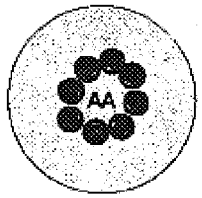
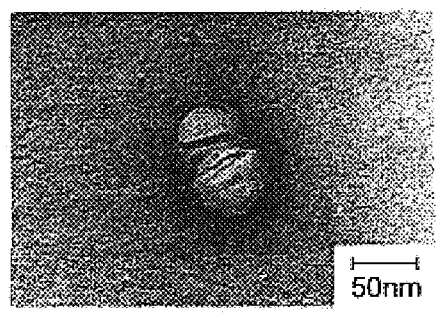

In paraffin the double-walled ascorbic acid micelle relinquishes its external shell.

Fig. 1

Product Micelle

For the first time the micelle (product micelle) has been rendered visible by electron microscope photographs in aqueous solution (1 : 1000) (produced at the Technical University of Darmstadt during work commissioned by AQUANOVA).

Vitamin A micelle in the water-soluble AQUANOVA retinol solubilisate

Vitamin E micelle in the water-soluble AQUANOVA tocopherol solubilisate

Substrate without micelles (carbon film)

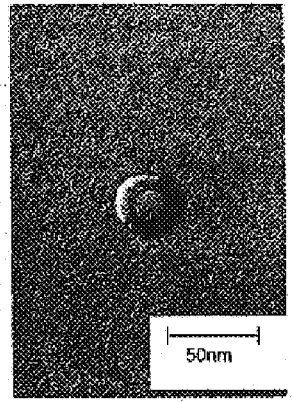

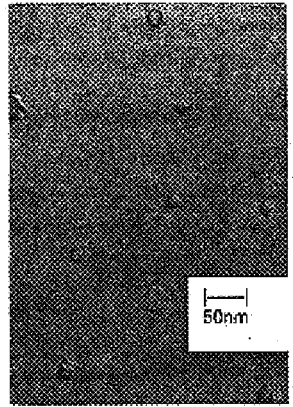

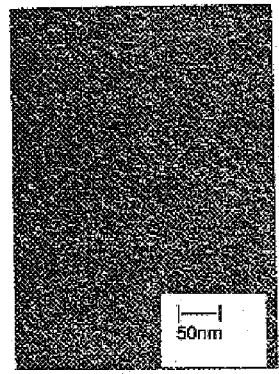

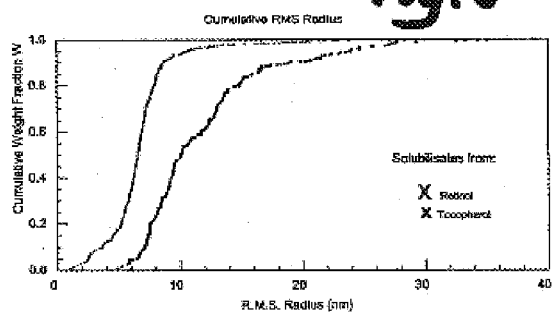

Radial distribution of micelles
AQUANOVA Vitamin E and
Vitamin A solubilisates in aqueous solution

AQUEOUS SOLUTION OF ASCORBIC ACID AND METHOD FOR PRODUCING SAME

BACKGROUND OF THE INVENTION

1. Field of the Invention

The invention refers to an aqueous solution of ascorbic acid.

2. Description of the Related Art

The technical use, in particular in personal hygiene and foodstuffs, and prophylactic application of the reductone, ascorbic acid, is often made more difficult in that the ascorbic acid is not sufficiently stable in aqueous solution. Consequently, in an aqueous ascorbic acid solution only about 70% of the added ascorbic acid is still present after 30 days.

Attempts have been made to improve the stability in that instead of ascorbic acid, one of its derivatives, for example sodium ascorbic phosphate or ascorbyl palmitate, has been employed. The content of this active substance is almost fully retained in aqueous solution over a long period of time. However, the derivative is many times more expensive than pure ascorbic acid. In addition, at higher concentrations the ascorbic acid derivatives tend to crystallize out and lead to colouration of the end product.

From the European Patent Specification 660676 a combination is known consisting of 0.1–2.0% by weight of an oil-soluble constituent which is preferably a colorizing carotenoid, 2–20% by weight of an emulsifier with an HLB value of 10–18 and 0.1–1.0% by weight of an antioxidation agent. The emulsifier can be Polysorbate 40 or 60 and ascorbic acid is one of the recommended antioxidation agents. With this technique, coloured clear and stable drinks for health care should be able to be produced. The stability of the ascorbic acid in the end product is however still not explained.

SUMMARY OF THE INVENTION

The object of the invention is to provide ascorbic acid in a fluid, water and fat-soluble and encapsulated form (e.g. gelatine capsule), which is stable over many months and is available in high concentration.

BRIEF DESCRIPTION OF THE DRAWINGS

FIG. 1: Schematics and electron micrographs of the micelle formed using a 10% ascorbic acid solubilisate in water and in paraffin are illustrate.

FIG. 5: A electron micrograph image of a Vitamin A micelle.

FIG. 6: A electron micrograph image of Vitamin E micelles, an electron micrograph image of the substrate without micelles, and a graph showing the mean micelle radii of the Vitamin A and Vitamin E solubilisates in aqueous solution.

DETAILED DESCRIPTION OF THE INVENTION

Figure 2:
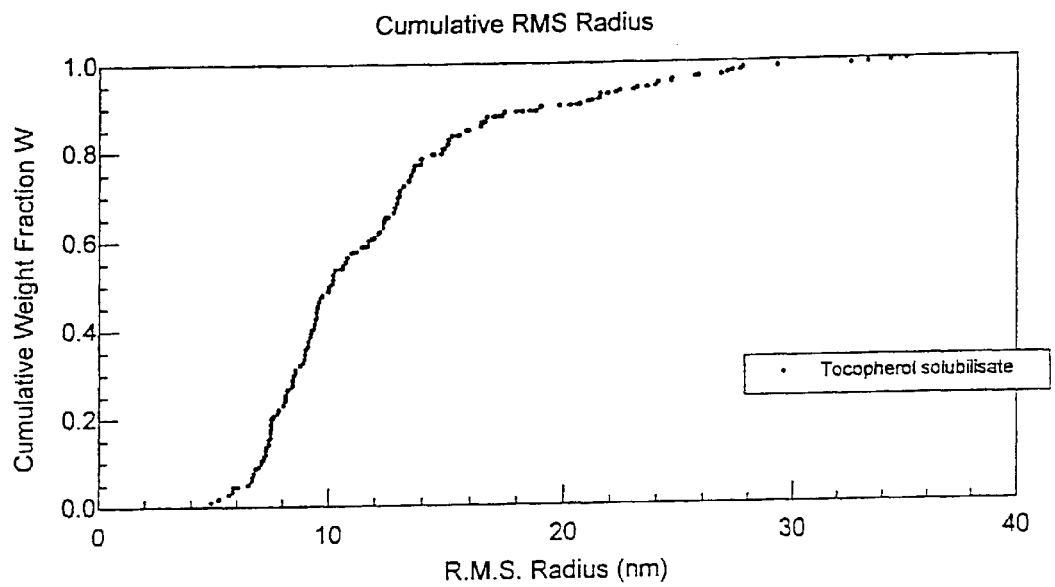
FIG. 2: A graph showing the mean micelle radii of the α-tocopherol solubilisate.
Figure 3:
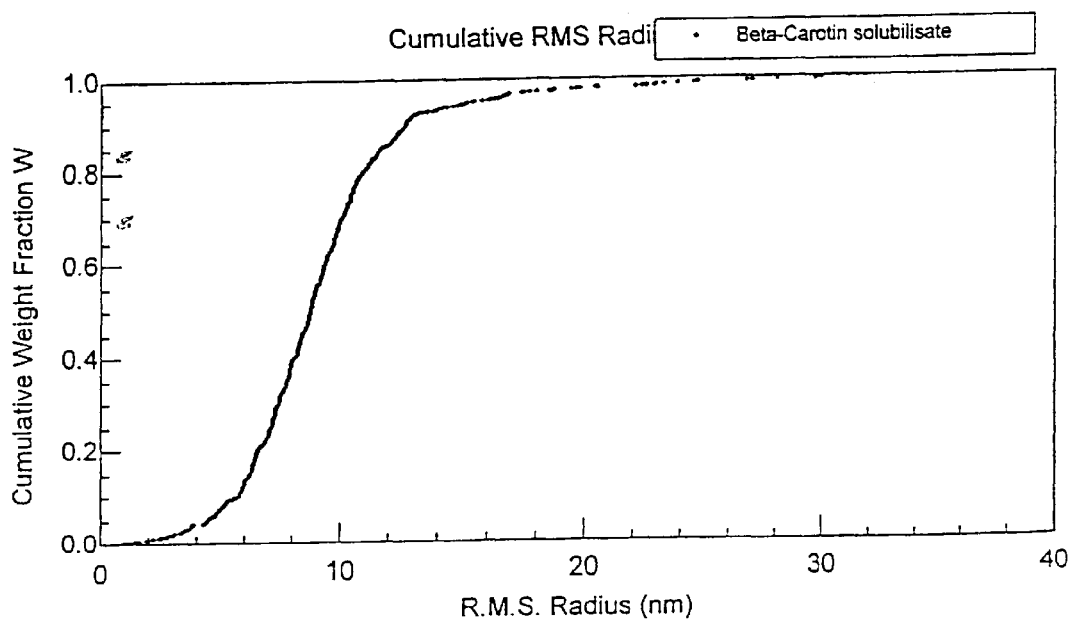
FIG. 3: A graph showing the mean micelle radii of the ⊕-carotene solubilisate.
Figure 4:
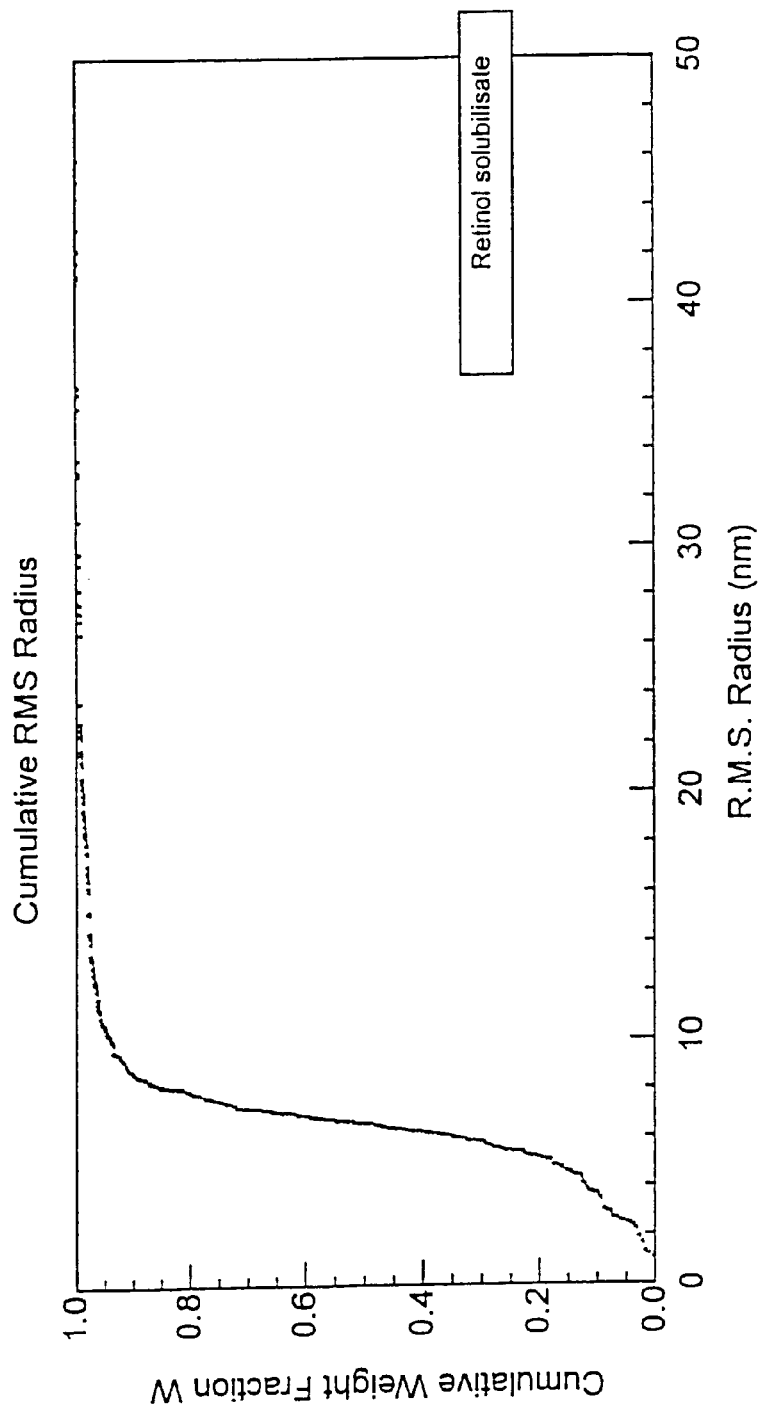
FIG. 4: A graph showing the mean micelle radii of the retinol solubilisate.

According to the invention, this object is resolved in that an aqueous solution of ascorbic acid contains an excess of an emulsifier with an HLB value of 9–18, such as a polysorbate, preferably Polysorbate 80. At room temperature the solution is clear and almost gel-like, can be diluted with water without becoming turbid and on heating to approximately 35° C. can be mixed, trouble-free and homogeneously with aqueous or fatty end products from the cosmetics or foodstuffs fields without further processing steps. The ascorbic acid part of the solution according to the invention, which may be up to 20% by weight, is retained over at least half a year almost without loss. The polysorbate part is effectively about 60% by weight and the rest is water. The ascorbic acid solubilisate according to the invention can be easily added to cosmetics (skin and hair care products), foodstuffs, medicaments and nutrient solutions for the breeding of cell and bacterial cultures as well as for algae (microalgae) with the result that the stability of these products is increased substantially.

The ascorbic acid is available micellated in the solubilisate. An electron microscope examination of a 10% ascorbic acid solubilisate in a dilution of 1:1000 exhibits a micelle diameter of about 100 nm. Since the emulsifier envelope of the micelles only releases the enclosed ascorbic acid with a delay (in a retarded manner), the antioxidative effect of the solubilisate according to the invention in the agents mentioned remains effective in combination with solubilised mixed tocopherols longer than of, say, ascorbyl palmitate, i.e. one of the ascorbic acid derivatives mentioned earlier.

Regarding the physiological aspects of nutrition, during the oral intake of the solubilisate according to the invention, the micellation of the ascorbic acid by the emulsifier prevents the ascorbic acid from developing its effect and being consumed already in the central digestive tract, i.e. in the stomach and duodenum. The micellated ascorbic acid is rather initially resorbed in the small intestine.

In a particularly preferred arrangement of the invention, the ascorbic acid solubilisate contains an addition of tocopherol, in particular a mix of α-, β-, γ- and δ-tocopherol. Through the addition of this ascorbic acid tocopherol solubilisate to organic oils, e.g. vegetable oils such as sunflower oil, thistle oil, linseed oil, etc., their stability can be substantially improved. As tocopherol, either pure α-tocopherol or, particularly preferred, a mixture of α-, β-, γ- and δ-tocopherol can be considered. Mixed tocopherols are recommended which contain about 8.0 to about 20.0% by weight of α-tocopherol, about 1.5 to about 4.5% by weight of β-tocopherol, about 55.0 to about 70.0% by weight of γ-tocopherol and about 15.0 to about 27.0% by weight of δ-tocopherol.

If an octadecatrienoic acid and/or an octadecenoic acid, say in the form of α-linolenic acid, γ-linolenic acid, linoleic acid or oleic acid, is added to the solution according to the invention, the viscosity of the solution is reduced. It is clear at room temperature, viscous, can be diluted with water without turbidity or can be mixed with aqueous and/or fatty nutriments, cosmetics and pharmaceuticals without further processing steps. The polysorbate content of the solution according to the invention develops a type of retarding function for the conservative characteristic of the ascorbic acid for the generally easily oxidizable ingredients of ointments and similar preparations. Consequently, the desired protective function of the ascorbic acid is retained over an extended period. The ascorbic acid content of the solution can effectively lie between 5% by weight to about 15% by weight. The solution can advantageously contain about 10% by weight to about 20% by weight of an octadecatrienoic acid and/or octadecenoic acid. The polysorbate part is preferably about 60% by weight to about 75% by weight.

If the proportion of water in the solution is reduced to between about 5% by weight to about 7% by weight and the polysorbate proportion is increased correspondingly, the solution, which is viscous at room temperature, can also be mixed with active substances which are then filled into gelatine capsules or gelatine-free capsules. The low proportion of water in the solution leaves the case of the capsule undamaged, whereby the protective function of the ascorbic acid for the active component remains unimpaired.

A procedure for the manufacture of the solution according to the invention provides that an emulsifier with an HLB value of about 9 to about 18, a polysorbate for example, effectively Polysorbate 80, is added to an aqueous ascorbic acid solution and the mixture is briefly heated with stirring until it becomes clear and homogeneous. The micelles forming in the solution and having a diameter of about 100 nm exhibit a double-walled envelope of radially orientated polysorbate molecules, whereby the polysorbate molecules of the inner envelope are aligned with their hydrophilic sections towards the ascorbic acid solution and the hydrophilic sections of the polysorbate molecules in the outer envelope are arranged towards the outside. The solution obtained in this manner can be diluted in water without becoming turbid and can be employed technically without further processing steps.

The stability of the micelles is increased if, in a further development of the invention, a light natural oil, mainly consisting of triglycerides, such as say thistle oil, is added to the aqueous ascorbic acid solution together with the emulsifier. The oil micelles which are then formed adhere to the ascorbic acid micelles and protect them.

Practically, an octadecatrienoic acid and/or an octadecenoic acid, say in the form of α-linolenic acid, γ-linolenic acid, linoleic acid or oleic acid, is added to the solution before the polysorbate is added and after slight heating to about 50° C. For the filling capsules, the cases of which consist of gelatine or which can be free of gelatine, it is advantageous if ascorbic acid is dissolved in the same quantity of distilled water, the same or up to a maximum of twice as much fatty acids as ascorbic acid is added under slight heating and approximately two to about three times the quantity of Polysorbate 80 added and the mixture heated to about 80° C. and stirred.

The following embodiment examples illustrate the invention.

EXAMPLE 1

20 g of ascorbic acid are completely dissolved in 20 g of distilled, degassed water. The dissolving stage can be speeded up if the water is heated to about 45° C. Then 60 g of Polysorbate 80 are added to the solution with stirring and heating to about 80° C. It is stirred until the solubilisate becomes clear and homogeneous, with the solubilisate appearing clear and almost gel-like at room temperature, dilutable in water without turbidity and can be added without further processing steps to compositions to be preserved or foodstuffs, drinks, cosmetics and pharmaceuticals.

For a less concentrated solubilisate, 10 g of ascorbic acid is dissolved in 10 g of distilled water and 80 g of Polysorbate is added, the remaining process being as above. From the 10% ascorbic acid solubilisate produced from this, an electron microscope image, which is reproduced in FIG. 1, was made after aqueous dilution of the solubilisate to 1:1000. It can be seen that the ascorbic acid solubilisate micelles have a diameter of about 100 nm. Putting the solubilisate in paraffin permits the micelle diameter to be reduced to half, as can be seen from the lower electron microscope image in FIG. 1. This phenomenon can be explained in that the micelles lose the outer polysorbate envelope in paraffin.

EXAMPLE 2

As in Example 1, 10% by weight of ascorbic acid (referred to the overall quantity of ascorbic acid solubilisate=100%) is dissolved in 10% by weight of distilled water and 70% by weight of Polysorbate 80 is added to this aqueous solution together with 10% by weight of a light vegetable oil, such as thistle oil or linseed oil. This is then heated to at least 60° C. and stirred until the solubilisate becomes clear and homogeneous with the solubilisate being dissolved clearly and without residue in water at room temperature.

If the content of ascorbic acid is reduced to about 7% by weight and the water content also to about 7% by weight and the other proportions of the solubilisate are increased accordingly, it can, due to the relatively low proportion of water, be particularly well employed as a preservative for active substances which are to be encapsulated as retard preparations. The capsule case is virtually left unattacked by the solubilisate which would be expected with a high water content.

EXAMPLE 3

10 g of ascorbic acid are dissolved in 10 g of distilled water and 20 g of thistle oil added to the solution. To this mixture 110 g of Polysorbate 80 are added, the whole stirred with heating at about 100° C. until free of water, i.e. until boiling terminates. After cooling to room temperature a 6.5% ascorbic acid solubilisate is present in the solubiliser, the water content of which is clearly below 5% by volume and which is both soluble in water as well as in fats and oils. Testing of the ascorbic acid content of the solution by an independent chemical examination laboratory at the time the solution was produced and more than five months later showed that the loss of ascorbic acid over this period was only about 3%.

EXAMPLE 4

Here, the starting point is the solubilisate according to Example 2. A mixed tocopherol solubilisate, which is produced in the following manner, is added to it. 10% by weight of mixed tocopherol (referred to the mixed tocopherol solubilisate=100% by weight) is mixed with 90% by weight of Polysorbate 20 by stirring, whereby the mixing process is speeded up by heating to about 60° C. Stirring is continued until clarity is obtained and the solubilisate can be easily dissolved in water. For the mixed tocopherol an addition of 91 mg/g of mixed tocopherol to α-tocopherol, 21 mg/g to β-tocopherol, 608 mg/g to γ-tocopherol and 209 mg/g to δ-tocopherol is recommended.

Then about 3 parts by weight of the solubilisate according to the first alternative in Example 2 are mixed with about 7 parts by weight of the mixed tocopherol solubilisate, whereby slight heating to about 50° C. speeds up the mixing process. Stirring under heat is carried out until an homogeneous and clear solubilisate is produced. Ig of this product therefore contains about 70 mg of mixed tocopherol and about 30 mg of ascorbic acid. This solubilisate can be employed as an effective antioxidant for the improvement of the stability of foodstuff colorants, oils, cosmetics, pharmaceuticals and similar products.

Comparative tests show that, independent of the properties of the end product (hydrophilic or hydrophobic) this solubilisate can be incorporated into end products directly and without intermediate production steps and offers better protection against oxidation then the same quantity of ascorbic acid from an ascorbic acid derivative, such as for example ascorbyl palmitate. Also, the relative lack of colour in the solubilisate in comparison to the ascorbic acid derivatives represents an advantage. Depending on requirements, for example, 1 to 10 g of solubilisate can be added to about 1000 g of the end product.

From a nutritional point of view, the physiological advantage of this solubilisate lies in the micelles which are stable in gastric acid and which ensure that ascorbic acid (Vitamin C) and (with the use of α-tocopherol) Vitamin E reach the small intestine without loss where they can be resorbed. This advantage can also be exploited for other vitamins, for example retinol (Vitamin A) and β-carotene, and can be obtained with the following example of a multi-vitamin preparation:

EXAMPLE 5

20% by weight of α-tocopherol, under heat as required at about 50° C., are mixed with 80% by weight of Polysorbate 20 until clarity and homogeneity are obtained through stirring.

10% by weight of retinol is mixed in the same manner with 90% by weight of Polysorbate 80.

Finally, 10% by weight of a concentrate, which contains about 30% of β-carotene (obtainable from La Roche), is mixed with 90% by weight of Polysorbate 80 in an appropriate manner to form a reddish brown, transparent solubilisate which dissolves clearly in warm water.

Then 85% by weight of the ascorbic acid solubilisate according to the first alternative in Example 2 is effectively mixed with 10% by weight of the above α-tocopherol solubilisate and with 2% by weight of the above retinol solubilisate and finally with 3% by weight of the β-carotene solubilisate under slight heat while stirring until a homogeneous and transparent mixed solubilisate is obtained. This water-soluble vitamin solubilisate can be packaged in gelatine or gelatine-free capsules or directly incorporated into aqueous and/or fat-soluble end products without additional processing steps.

When put into water and/or clear fruit juice, the vitamin solubilisate according to the invention gives a stable and clear solution, in contrast to emulsions or liposomes. The product micelles are stable in gastric acid. The resorption of the fat-soluble substances located in the micelles, such as Vitamin A, Vitamin E and β-carotene occurs in the small intestine without involving bile salts and enzymes. Consequently, the quoted active substances in this micellated form are more quickly biologically available.

1 g of the vitamin solubilisate with the above composition and incorporated into foodstuffs or packaged in capsules covers the human daily requirement of Vitamins A, C, E and β-carotene. The composition of the vitamin solubilisate quoted with the figures above is geared to this application. This takes into account that the daily requirement of Vitamin C is substantially higher than for the other vitamins. However, the scope of the invention also enables other compositions to be selected for the vitamin solubilisate and/or one or the other vitamin to be completely omitted if the presence of a certain vitamin is not required or desirable for the planned application.

What is claimed is:

1. Aqueous solution of ascorbic acid which contains an excess of an emulsifier with an HLB value of about 9 to about 18, for example a polysorbate.

2. Solution according to claim 1 containing Polysorbate 80.

3. Solution according to claim 1 which contains an octadecatrienoic acid and/or an octadecenoic acid, say in the form of α-linolenic acid, γ-linolenic acid, linoleic acid or oleic acid.

4. Solution according to claim 1 with an ascorbic acid content of about 20% by weight and a polysorbate content of about 60% by weight.

5. Solution according to claim 3 with an ascorbic acid content of about 5% by weight to about 15% by weight, a polysorbate content of about 75% by weight to about 60% by weight and an octadecatrienoic acid and/or octadecenoic acid content of about 10% by weight to about 20% by weight.

6. Solution according to claim 1 and containing some mixed tocopherol.

7. Solution according to claim 6 containing some Polysorbate 20.

8. Solution according to claim 6 containing about 8 to about 20% by weight of α-tocopherol, about 1.5 to about 4.5% by weight of β-tocopherol, about 55 to about 70% by weight of γ-tocopherol and about 15 to about 27% by weight of δ-tocopherol.

9. Solution according to claim 1 containing Vitamin A, and/or Vitamin E and/or β-carotene.

10. Procedure for the manufacture of a solution according to claim 1 characterised in that a polysorbate is added to an aqueous ascorbic acid solution and the mixture is, where appropriate, stirred under slight heat until it becomes clear.

11. Procedure according to claim 10, characterised in that Polysorbate 80 is added to the solution.

12. Procedure according to claim 10, characterised in that an octadecatrienoic acid and/or an octadecenoic acid, say in the form of α-linolenic acid, γ-linolenic acid, linoleic acid or oleic acid, is added to the solution before the polysorbate is added and after slight heating to about 50° C. with stirring.

13. Procedure according to claim 10 in which a quantity of ascorbic acid is dissolved in the same quantity of distilled water, a quantity of light, fatty acids containing triglycerides and equal to double the quantity of ascorbic acid is added under slight heating and about two to about three times the quantity of Polysorbate 80 is added and the mixture heated to about 80° C. with stirring.

14. Procedure according to claim 10, characterised in that a mixture of α-tocopherol and Polysorbate 20, which has been stirred to clarity, where appropriate under slight heating, is added to the solution.

15. Procedure according to claim 10, characterised in that a mixture of retinol and Polysorbate 80, stirred to clarity is added.

16. Procedure according to claim 10, characterised in that a mixture of β-carotene and Polysorbate 80, stirred to clarity, is added.

17. Application of a solution according to claim 1 as additive in skin and hair-care products, foodstuffs, medicaments and nutrient solutions for cell and bacterial cultures or algae cultures.

* * * * *